United States Patent [19]

Michelson

[11] Patent Number: 5,609,635

[45] Date of Patent: Mar. 11, 1997

[54] LORDOTIC INTERBODY SPINAL FUSION IMPLANTS

[76] Inventor: Gary K. Michelson, 438 Sherman Canal, Venice, Calif. 90291

[21] Appl. No.: 482,146

[22] Filed: Jun. 7, 1995

Related U.S. Application Data

[63] Continuation-in-part of Ser. No. 263,952, Jun. 22, 1994, abandoned, which is a continuation of Ser. No. 52,211, Apr. 22, 1993, abandoned, which is a continuation of Ser. No. 546,849, Jul. 2, 1990, abandoned, which is a continuation of Ser. No. 212,480, Jun. 28, 1988, abandoned.

[51] Int. Cl.$^6$ ..................................................... A61F 2/44
[52] U.S. Cl. ................................................ 623/17; 606/61
[58] Field of Search ................................ 623/17; 606/60, 606/61

[56] References Cited

U.S. PATENT DOCUMENTS

| | | | |
|---|---|---|---|
| 3,867,728 | 2/1975 | Stubstad et al. | 623/17 |
| 4,501,269 | 2/1985 | Bagby | 606/61 |
| 4,834,757 | 5/1989 | Brantigan | 623/17 |
| 5,306,309 | 4/1994 | Wagner et al. | 623/17 |

FOREIGN PATENT DOCUMENTS

| | | | |
|---|---|---|---|
| 599419 | 6/1994 | European Pat. Off. | 623/17 |

*Primary Examiner*—Randy O. Shay
*Attorney, Agent, or Firm*—Lewis Anten, Esq.; Amedeo Ferraro, Esq.

[57] ABSTRACT

The present invention is directed to interbody spinal fusion implants having a structural configuration that provides for the maintaining and creating of the normal anatomic angular relationship of two adjacent vertebrae of the spine to maintain and create spinal lordosis. The spinal fusion implants of the present invention are sized to fit within the disc space created by the removal of disc material between two adjacent vertebrae and conform wholly or in part to the disc space created. The spinal fusion implants of the present invention have upper and lower surfaces that form a support structure for bearing against the end plates of the adjacent vertebrae. The upper and lower surfaces are disposed in a converging angular relationship to each other such that the implants of the present invention have an overall "wedged-shape" in an elevational side view. The angular relationship of the upper and lower surfaces places and maintains the vertebrae adjacent to those surfaces in an angular relationship to each other, creating and maintaining the desired lordosis.

51 Claims, 10 Drawing Sheets

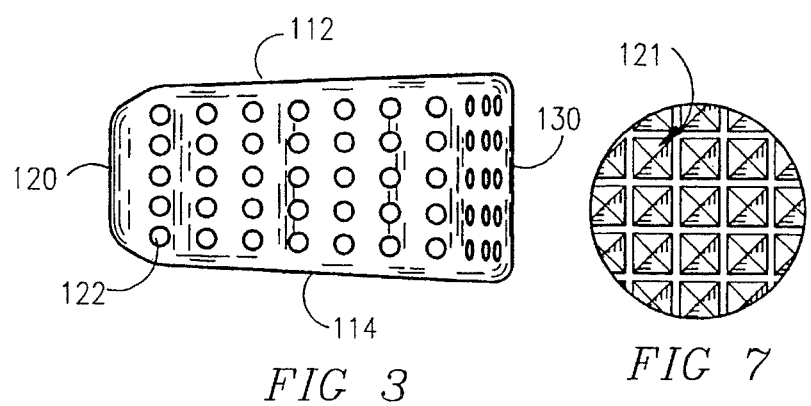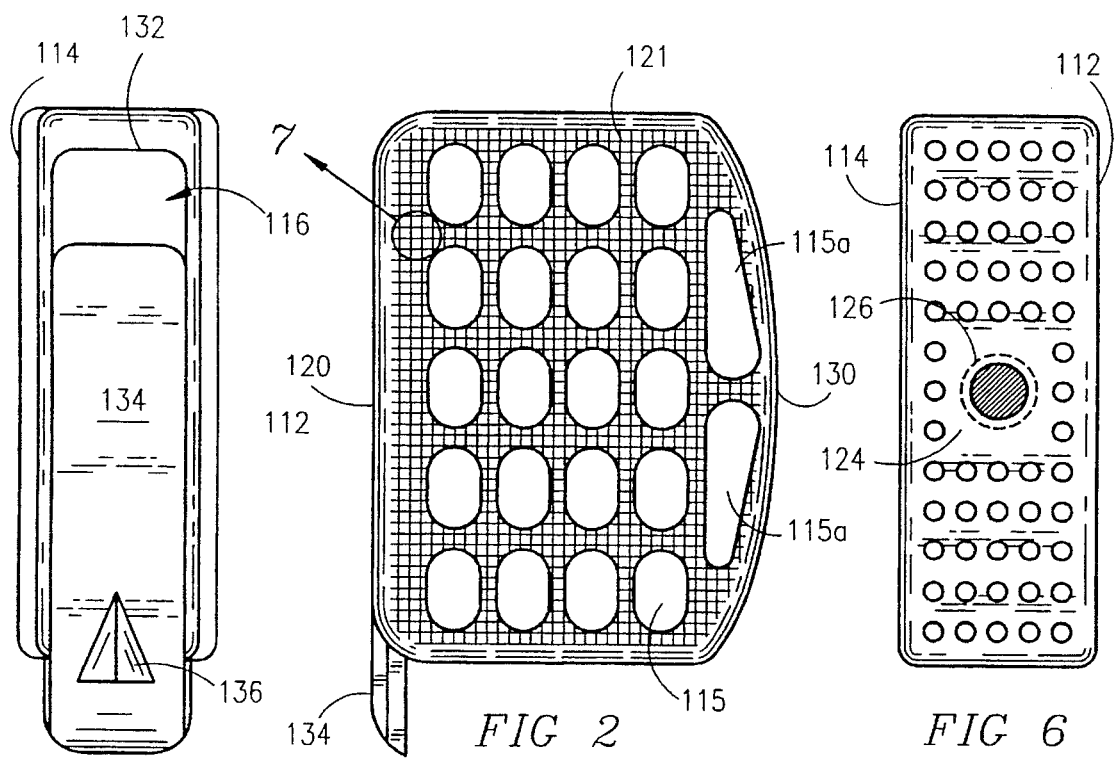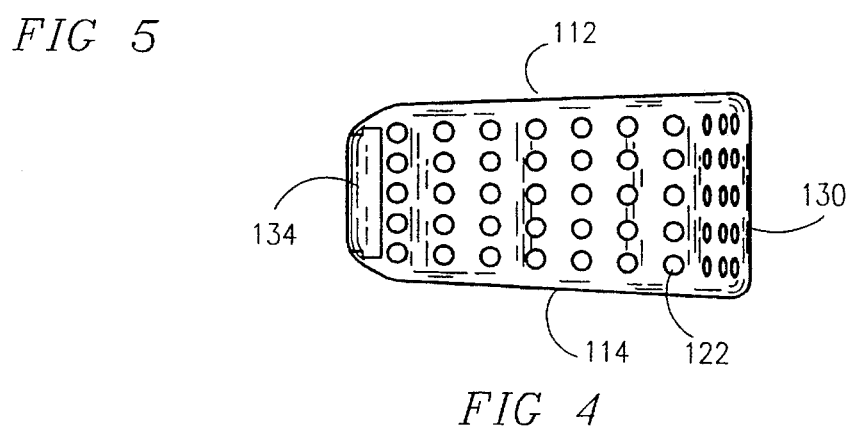

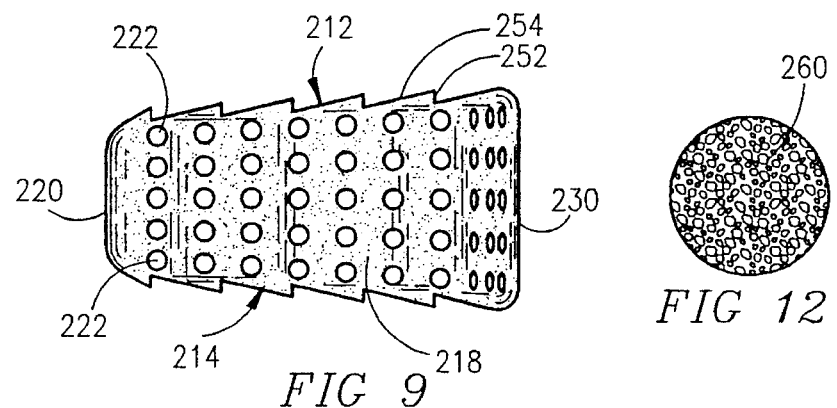
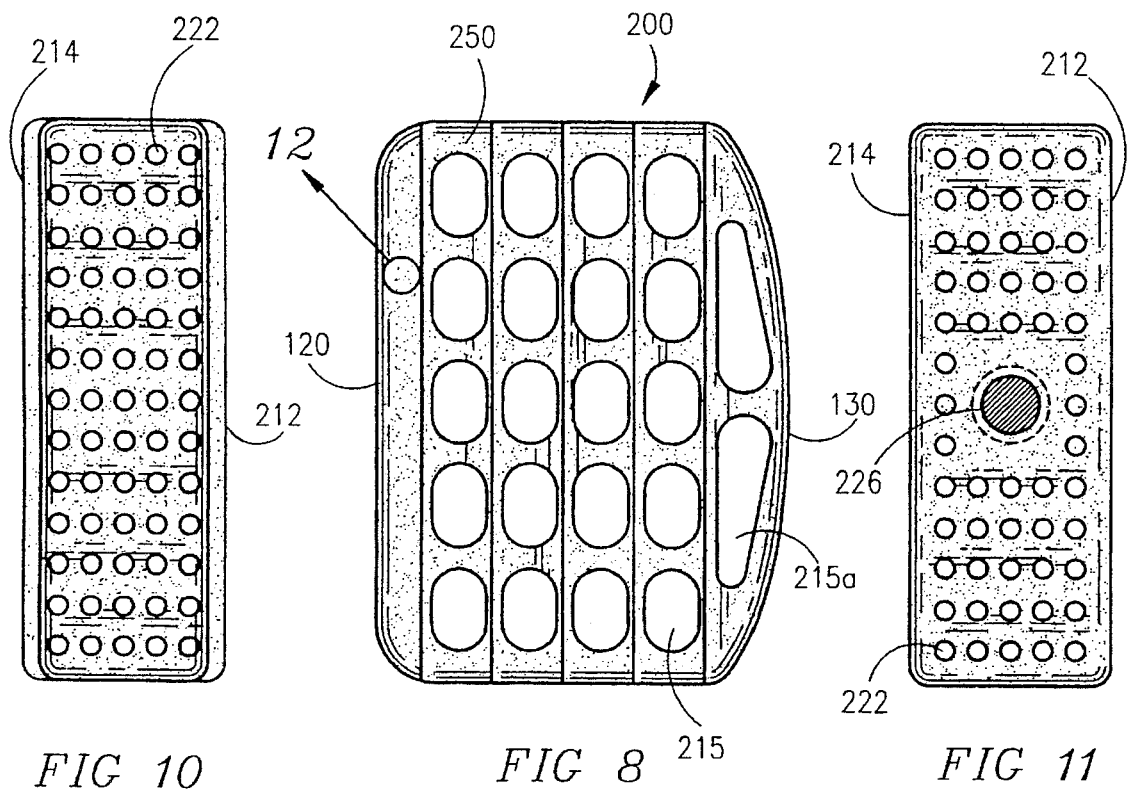

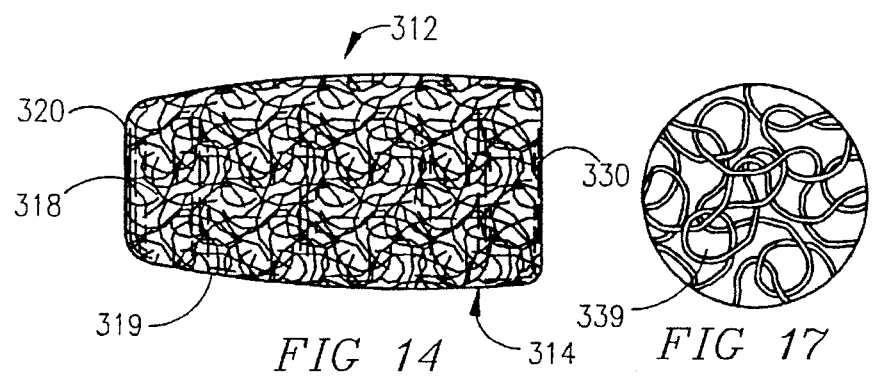
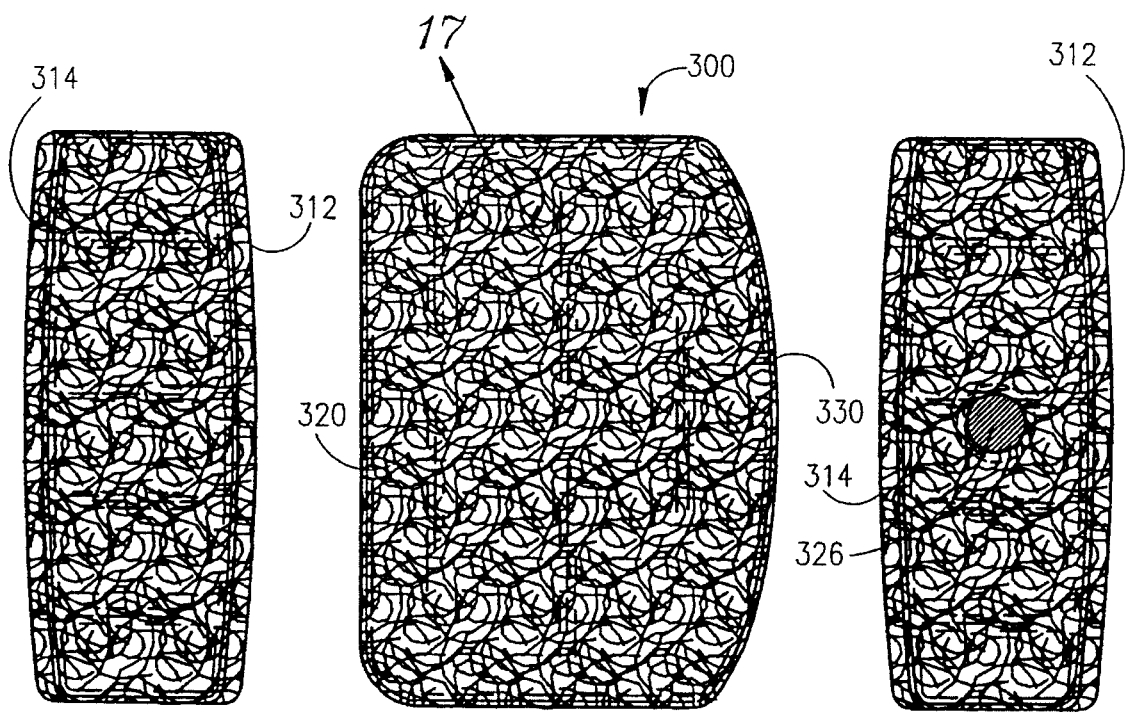
FIG 14  FIG 17
FIG 15  FIG 13  FIG 16

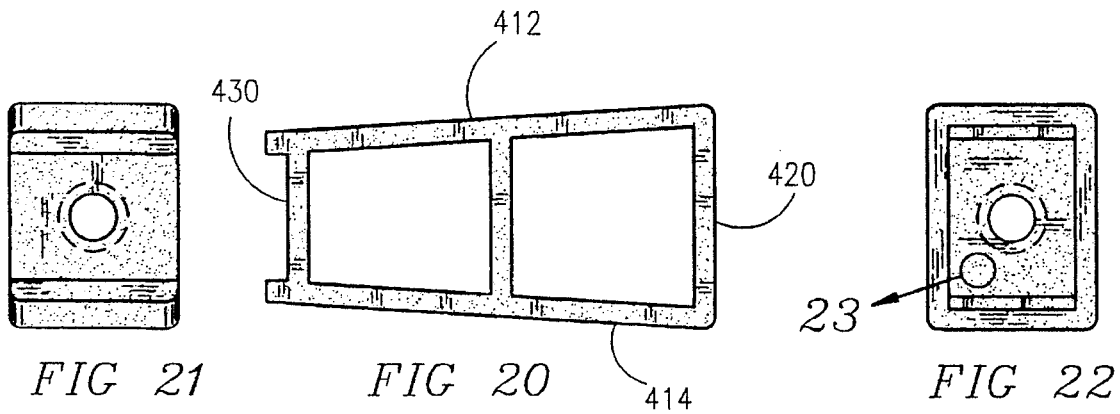
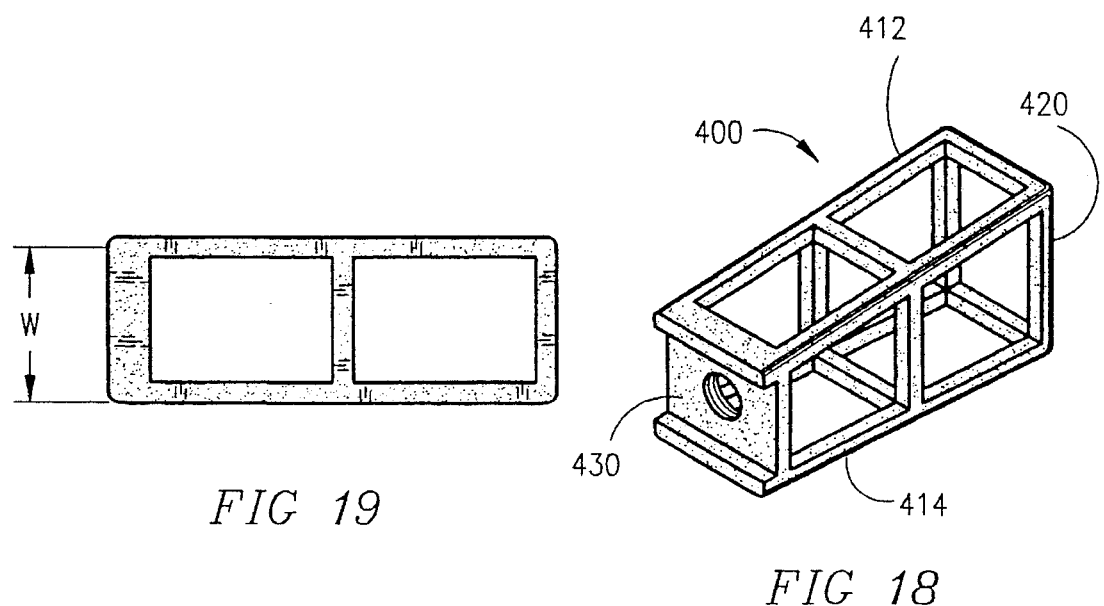
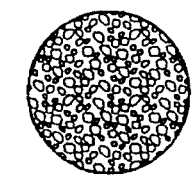

LORDOTIC INTERBODY SPINAL FUSION IMPLANTS

BACKGROUND OF THE INVENTION

RELATED APPLICATION

This application is a continuation in part of U.S. application Ser. No. 08/263,952 filed on Jun. 22, 1994, now abandoned, which is a continuation of application Ser. No. 08/052,211 filed on Apr. 22, 1993, now abandoned which is a continuation of application Ser. No. 07/546,849, filed on Jul. 2, 1990, now abandoned, which is a continuation of application Ser. No. 07/212,480 filed on Jun. 28, 1988, now abandoned.

FIELD OF THE INVENTION

The present invention relates generally to interbody spinal fusion implants, and in particular to spinal fusion implants configured to restore and maintain two adjacent vertebrae of the spine in correct anatomical angular relationship.

DESCRIPTION OF THE RELATED ART

Both the cervical and lumbar areas of the human spine are, in a healthy state, lordotic such that they are curved convex forward. It is not uncommon that in degenerative conditions of the spine that lordosis is lost. This effectively shortens the spinal canal which decreases its capacity. Further, the absence of lordosis moves the spinal cord anteriorly where it may be compressed against the posterior portions of the vertebral bodies and discs. Finally, such a loss of lordosis disturbs the overall mechanics of the spine which may cause cascading degenerative changes throughout the adjacent spinal segments.

The surgical treatment of those degenerative conditions of the spine in which the spinal discs are in various states of collapse, and out of lordosis, commonly involves spinal fusion. That is the joining together of adjacent vertebrae through an area of shared bone. When the shared bone is in the area previously occupied by the intervertebral disc that is referred to as an interbody fusion. Further history in this regard is provided in application Ser. No. 08/263,952 entitled Artificial Spinal Fusion Implants ("Parent Application") incorporated herein by reference.

The Parent Application taught the use of artificial spinal fusion implants that were capable of being placed between adjacent vertebrae, and which implants were capable of containing and providing fusion promoting substances including bone at the fusion site. These devices were further capable of restoring the height of the disc space and of supporting the spine, and were self-stabilizing as well as being stabilizing to the spinal area where implanted.

SUMMARY OF THE INVENTION

The present invention is directed to interbody spinal fusion implants having a structural configuration that provides for the maintaining and creating of the normal anatomic angular relationship of two adjacent vertebrae of the spine to maintain and create spinal lordosis. The spinal fusion implants of the present invention are sized to fit within the disc space created by the removal of disc material between two adjacent vertebrae and conform wholly or in part to the disc space created. The spinal fusion implants of the present invention have upper and lower surfaces that form a support structure for bearing against the end plates of the adjacent vertebrae. In the preferred embodiments, the upper and lower surfaces are disposed in a converging angular relationship to each other such that the implants of the present invention have an overall "wedged-shape" in an elevational side view. The angular relationship of the upper and lower surfaces places and maintains the vertebrae adjacent to those surfaces in an angular relationship to each other, creating and maintaining the desired lordosis.

The implants of the present invention may have surface irregularities to increase their surface area, and/or to further engage the adjacent vertebrae and to enhance stability. The lordotic implants of the present invention may have surface irregularities that are uniform in height along the longitudinal axis of the upper and lower vertebrae engaging surfaces, or may increase in height from one end of the implant to the other. That is, the implant body and the surface formed and the projections may be similarly wedged. The outer contour of the surface projections may be more or less rectangular while the underlying implant may be wedge-shaped; or the reverse wherein the underlying implant body is more or less rectangular while the contour of the surface projections are wedge-shaped from one end of the implant to the other.

The implants of the present invention have various faces which may be curved so as to conform to the shape of the vertebral surfaces adjacent to the area of the disc removal. Specifically the upper and/or lower surfaces may be convex, and/or the front and/or rear surfaces may be convex. The surfaces of the implants of the present invention may have openings which may or may not pass all the way through them, and a central chamber in communication to the surface through holes. The openings may be of random sizes, and/or shapes, and/or distributions. The implants themselves may be composed of materials, and/or have surface treatments, to encourage microscopic bone ingrowth into the implants.

In the performing of a posterior lumbar interbody fusion, it is not possible to replace the removed portions of the disc, if a total nuclear discectomy has been performed, with a single large implant as the delicate dural sac containing the spinal cord, and the nerve roots cover at all times at least some portion of the posterior disc space. As set forth in the Parent Application, the use of "modular implants" is appropriate in such cases. The modular implants being approximately as long as the depth of the disc material removed, but being considerably narrower, such that they can be introduced into the disc space from the posterior aspect to either side of the dural sac, and then aligned side to side within the disc space so that a number of them each having a length consistent with the depth of the disc removed in that area would in combination have a width equal to the width of the disc material removed.

The modular implants of the present invention may be generally wedge-shaped and may have upper and lower surfaces conforming to the contours of the vertebral end-plates, which contours include but are not limited to being relatively flat or convex. As the disc spaces in the lumbar spine are generally lordotic, said implants in the preferred embodiment would be taller anteriorly, that is at the implant's insertion end, and less tall posteriorly, that is at the implant's trailing end. To introduce an implant that is taller at its insertion end than the space available at the posterior aspect of the disc space, even when that disc space is optimally distracted, is problematic.

The modular implants of the present invention provide two solutions to the problem. In the first embodiment, the modular implants may have a reduced size at their insertion end, including but not limited to a bullet nose, a convexity, and a chamfer to a smaller front surface. This then provides that the implant has an area small enough to be introduced into the posterior aspect of the disc space when the disc space is adequately distracted and the contour of that specialized leading portion of the implant is such that it then allows for a ramping up of the adjacent vertebrae relative to the implant as the implant is advanced forward into the disc space.

The implants of the present invention provide a second solution to this same problem. In the preferred embodiment of the modular implant, the implant is again wedge-shaped in the side elevational view and is taller at its insertion end than at its trailing end. However, the implant incorporates at its trailing end a means for engaging insertion instrumentation such as the box and threaded opening configuration disclosed in the Parent Application. Since in the preferred embodiment these implants are wedge-shaped in the side elevational view when upright but are generally rectangular when viewed from the top plan view, these implants are therefore designed to be introduced into the disc space on their side such that the side walls of the implants are adjacent to the end plates of the adjacent vertebrae. The implants have a side-to-side dimension that is less than the dimension through the insertion end of the implant when upright. It is possible to easily insert these implants with them on their side and then to use the insertion instrument engaged to the implant to rotate the implants ninety degrees into the fully upright position, once they have been fully inserted. Once inserted, the upper and lower surfaces are adjacent to the endplates of the adjacent vertebrae and create and maintain the desired angular relationship of the adjacent vertebrae as the upper and lower walls are angled with respect to each other.

In an alternative embodiment of the present invention, a mechanical implant which may be inserted in a collapsed position and which may then be adjusted to increase in height so as to provide for the optimal restoration of the height of the space between the adjacent vertebrae is disclosed. The mechanical implant may be wedge-shaped, and have upper and lower surfaces, the contours of which generally conform to the contacted areas of the adjacent vertebral endplates and which contours may include but are not limited to being relatively flat, or convex. Further, the mechanical implant may be wedge-shaped or generally rectangular, but capable of increasing in both height and the extent of wedging when adjusted. This may easily be achieved by having one of the two wedge mechanisms employed in the example given being larger, or steeper than the other. Alternatively, a single wedge may be utilized, and if it is desired to achieved increased height at one end of the implant while restricting the height at the other, then the end of the implant may incorporate a hinge means and the height expansion at the other end achieved by drawing a wedge member, bar, ball, or other means from the far end toward the hinged end so as to drive said upper and lower surfaces apart in a wedged fashion.

In an alternative embodiment of the present invention, an implant having a mechanically deployable bone engaging means is taught. Such an implant is generally wedge-shaped in the side elevational view and has upper and lower surfaces generally conforming to the contour of the vertebral endplates where contacted by the implant, and which upper and lower surfaces may be but are not limited to being either flat or convex. The use of such deployable bone engaging means are particularly of value in that the largest possible implant may be inserted into a disc space and the vertebral engaging means, which if fixed to the surface would have blocked the insertion of the implant, may then be deployed after the insertion such that the distance from the tip of the upper and lower bone engagement means exceeds the height of the space available for insertion. Such a feature is of particular value when the implant itself is wedge-shaped as the considerable compressive loads across the lumbar spine would tend to drive a wedge-shaped implant out of the disc space.

OBJECTS OF THE PRESENT INVENTION

It is an object of the present invention to provide a spinal fusion implant that is easily inserted into the spine, having a tapered leading end;

It is another object of the present invention to provide a spinal fusion implant that tapers in height from one end to the other consistent with the taper of a normal spinal disc;

It is yet another object of the present invention to provide a spinal fusion implant that is capable of maintaining anatomic alignment and lordosis of two adjacent vertebrae during the spinal fusion process;

It is still another object of the present invention to provide a spinal fusion implant that is self stabilizing within the spine;

It is yet another object of the present invention to provide a spinal fusion implant that is capable of providing stability between adjacent vertebrae when inserted;

It is further another object of the present invention to provide a spinal fusion implant that is capable of spacing apart and supporting adjacent vertebrae in an angular relationship during the spinal fusion process;

It is still further another object of the present invention to provide a spinal fusion implant that fits between to adjacent vertebrae and preserves the end plants of those vertebrae; and It is another object of the present invention to provide a spinal fusion implant having a shape which conforms to the endplates of the adjacent vertebrae; and These and other objects of the present invention will become apparent from a review of the accompanying drawings and the detailed description of the drawings.

BRIEF DESCRIPTION OF THE DRAWINGS

FIG. 2 is a top plan view of the lordotic interbody spinal fusion implant of the present invention.

FIG. 3 is a left side elevational view of the lordotic interbody spinal fusion implant of the present invention.

FIG. 4 is a right side elevational view of the lordotic interbody spinal fusion implant of the present invention.

FIG. 5 is a front end view of the lordotic interbody spinal fusion implant of the present invention showing the slidable door in a partially open position.

FIG. 6 is a rear end view of the lordotic interbody spinal fusion implant of the present invention showing the means for engaging insertion instrumentation.

FIG. 7 is an enlarged fragmentary view along line 7 of FIG. 2 illustrating the bone engaging surface configuration of the lordotic interbody spinal fusion implant of the present invention.

FIG. 8 is a top plan view of an alternative embodiment of the lordotic interbody spinal fusion implant of the present invention.

FIG. 9 is a left side elevational view of the lordotic interbody spinal fusion implant of FIG. 8.

FIG. 10 is a front end view of the lordotic interbody spinal fusion implant of FIG. 8.

FIG. 11 is a rear end view of the lordotic interbody spinal fusion implant of FIG. 8 showing the means for engaging insertion instrumentation.

FIG. 12 is an enlarged fragmentary view along line 12 of FIG. 8 illustrating the surface configuration the lordotic interbody spinal fusion implant of the present invention.

FIG. 13 is a top plan view of an alternative embodiment of the lordotic interbody spinal fusion implant of the present invention made of a mesh-like material.

FIG. 14 is a left side elevational view of the lordotic interbody spinal fusion implant of FIG. 13.

FIG. 15 is a front end view of the lordotic interbody spinal fusion implant of FIG. 13.

FIG. 16 is a rear end view of the lordotic interbody spinal fusion implant of FIG. 13 showing the means for engaging insertion instrumentation.

FIG. 17 is an enlarged fragmentary view along line 17 of FIG. 13 illustrating the surface configuration of the lordotic interbody spinal fusion implant of the present invention.

FIG. 18 is a perspective view of an alternative embodiment of the lordotic interbody spinal fusion implant of the present invention.

FIG. 19 is a top plan view of the lordotic interbody spinal fusion implant of FIG. 18.

FIG. 20 is a left side elevational view of the lordotic interbody spinal fusion implant of FIG. 18.

FIG. 21 is a rear end view of the lordotic interbody spinal fusion implant of FIG. 18.

FIG. 22 is a front end view of the lordotic interbody spinal fusion implant of FIG. 18.

FIG. 23 is an enlarged fragmentary view along line 23 of FIG. 18 illustrating the surface configuration the lordotic interbody spinal fusion implant of the present invention.

DETAILED DESCRIPTION OF THE DRAWINGS

Figure 1:
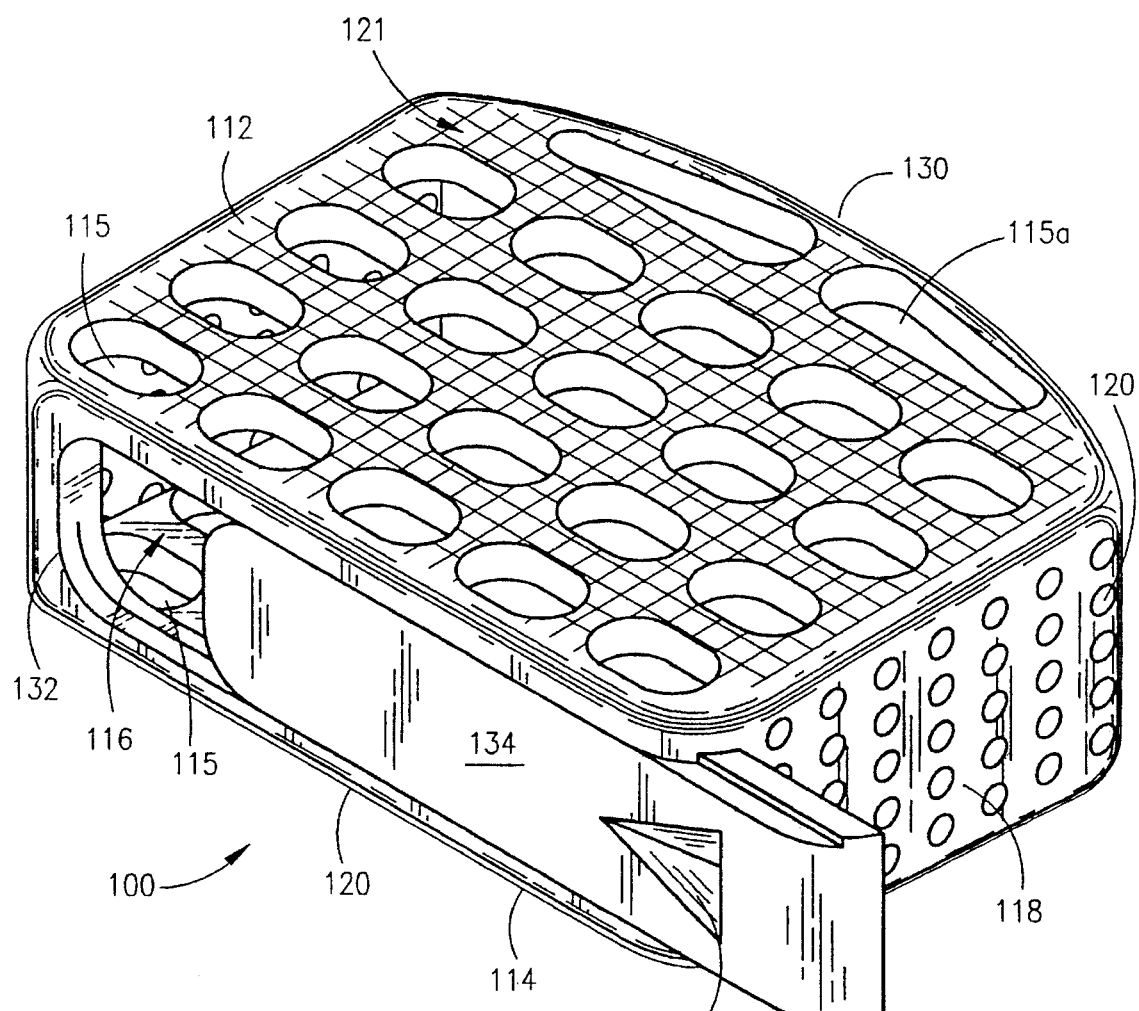
FIG. 1 is a perspective view of the lordotic interbody spinal fusion implant of the present invention with a slidable door shown in a partially open position providing access to the internal chamber of the implant.

Referring to FIGS. 1 through 7 the lordotic interbody spinal fusion implant of the present invention for use in the disc space between two adjacent vertebrae, generally referred to by the numeral 100, is shown. The implant 100 has a generally rectangular configuration, having an upper surface 112 and a lower surface 114. In the preferred embodiment, the upper and lower surfaces 112 and 114 of implant 100 are disposed in a converging angular relationship toward each other such that the implant 100 appears "wedge-shaped" from a side elevational view as shown in FIGS. 3 and 4. The upper and lower surfaces 112 and 114 have an interior surface which form a support structure for bearing against the endplates of the adjacent vertebrae between which the implant 100 is inserted. The angular relationship of the upper and lower surfaces 112 and 114 places and maintains the vertebrae adjacent to those surfaces in an angular relationship, creating and maintaining the desired lordosis of the spine.

The upper and lower surfaces 112 and 114 of the implant 100 may be flat or curved to conform to the shape of the end plates of the adjacent vertebrae between which the implant 100 is inserted. The implant 100 conforms to the shape of the nucleus pulposus and a portion of the annulus fibrosus removed from the vertebrae. The upper and lower surfaces 112 and 114 comprise surface roughenings that provide a surface suitable for engaging the adjacent vertebrae to stabilize the implant 100 within the disc space once surgically implanted. The surface roughenings of the upper and lower surfaces 112 and 114 comprise a surface knurling 121.

Referring to FIG. 7, an enlarged fragmentary view of the surface knurling 121 of the implant 100 is shown as a diamond-shaped bone engaging pattern. The implant 100 may have surface knurling 121 throughout the entire upper and lower surfaces 112 and 114, throughout only a portion of the upper and lower surfaces 112 and 114, or any combination thereof, without departing from the scope of the present invention. It is also appreciated that the surface knurling 121 may have various configuration other than the configuration shown.

In this embodiment, the implant 100 is hollow and comprises a plurality of openings 115 of passing through the upper and lower surfaces 112 and 114 and into a central hollow chamber 116. The openings 115 provide for bone growth to occur from the vertebrae through the openings 115 to the internal chamber 116. While the openings 115 have been shown in the drawings as being circular, it is appreciated that the openings 115 may have any shape, size, configuration or distribution suitable for use in a spinal implant without departing from the scope of the present invention. For example, the openings may have a tear-drop configuration as shown in opening 115a in FIGS. 1 and 2.

The upper and lower surfaces 112 and 114 of the implant 100 are supported and spaced apart by a side wall 118, which may also comprise a plurality of openings 122.

The implant 100 has an insertion end 120 and a trailing end 130 both of which may be curved or flat. The trailing end 130 of the implant may be convex to conform to the curvature of the vertebrae and has a means for engaging an implant insertion instrument comprising a depressed portion 124 with a central threaded opening 126 for receiving the engaging end of a driving instrument. The insertion end 120 of the implant 100 comprises an access opening 132 and a slidable door 134 which closes the opening 132. The slidable door 134 covers the opening 132 into the chamber 116 and permits the insertion of autogenous bone material into the chamber 116.

In use, the slidable door 134 is placed in the open position for loading material into the chamber 116. The slideable door 134 has a depression 136 for facilitating the opening and closing of the door 134. The internal chamber 116 can be filled and hold any natural or artificial osteoconductive, osteoinductive, osteogenic, or other fusion enhancing material. Some examples of such materials are bone harvested from the patient, or bone growth inducing material such as, but not limited to, hydroxyapatite, hydroxyapatite tricalcium phosphate; or bone morphogenic protein. The implant 100 itself is made of material appropriate for human implantation such as titanium and/or may be made of, and/or filled and/or coated with a bone ingrowth inducing material such as, but not limited to, hydroxyapatite or hydroxyapatite tricalcium phosphate or any other osteoconductive, osteoinductive, osteogenic, or other fusion enhancing material.

The fusion enhancing material that is packed within the chamber 116 of the implant 10 serves to promote bone ingrowth between the implant 100 and the adjacent vertebrae. Once the bone ingrowth occurs, the implant 100 will be a permanent fixture preventing dislodgement of the implant as well as preventing any movement between the adjacent vertebrae.

The slidable door 134 is then closed prior to implantation. In the closed position, the slideable door conforms to the curvature of the insertion end 120 of the implant 100. Various methods of packing the implant 100 with the autogenous bone material may be used to obtain a completely packed implant 100.

The method of inserting the implant 100 is set forth in detail in application Ser. No. 08/263,952, incorporated herein by reference. The threaded end of a driving instrument is attached to the threaded opening 126 in the trailing end 120 of the implant 100 and the fitting of the driving instrument into the depressed portion 124 prevents movement of the implant 100 in relationship to the driving instrument. The implant 100 is then placed at the entrance to the disc space between the two adjacent vertebrae V. The driver instrument is then tapped with a hammer sufficiently hard enough to drive the implant 100 into the disc space.

The size of the implant 100 is substantially the same size as the disc material that it is replacing and thus will be larger or smaller depending on the amount of disc material removed to create the disc space in which it is to be used. In the preferred embodiment in regard to the lumbar spine the implant 100 is approximately 28–48 mm wide, approximately 36 mm being preferred. The implant 100 has a height conforming to the restoration of the anatomic height of the disc space the average height would range from 8–16 mm, with 10–12 of which being the preferred average height. The depth would at its maximum range from 20 to 34 mm with 26 to 32 being the preferred maximum depth. In the cervical spine the width of the implant is in the range of approximately 14–28 mm, with the preferred width being 18–22 mm. The implant has a height in the range of approximately 5–10 mm with the preferred height being 6–8 mm. The implant has a depth in the range of approximately 11–21 mm with the preferred depth being 11–13 mm.

Figure 7A:
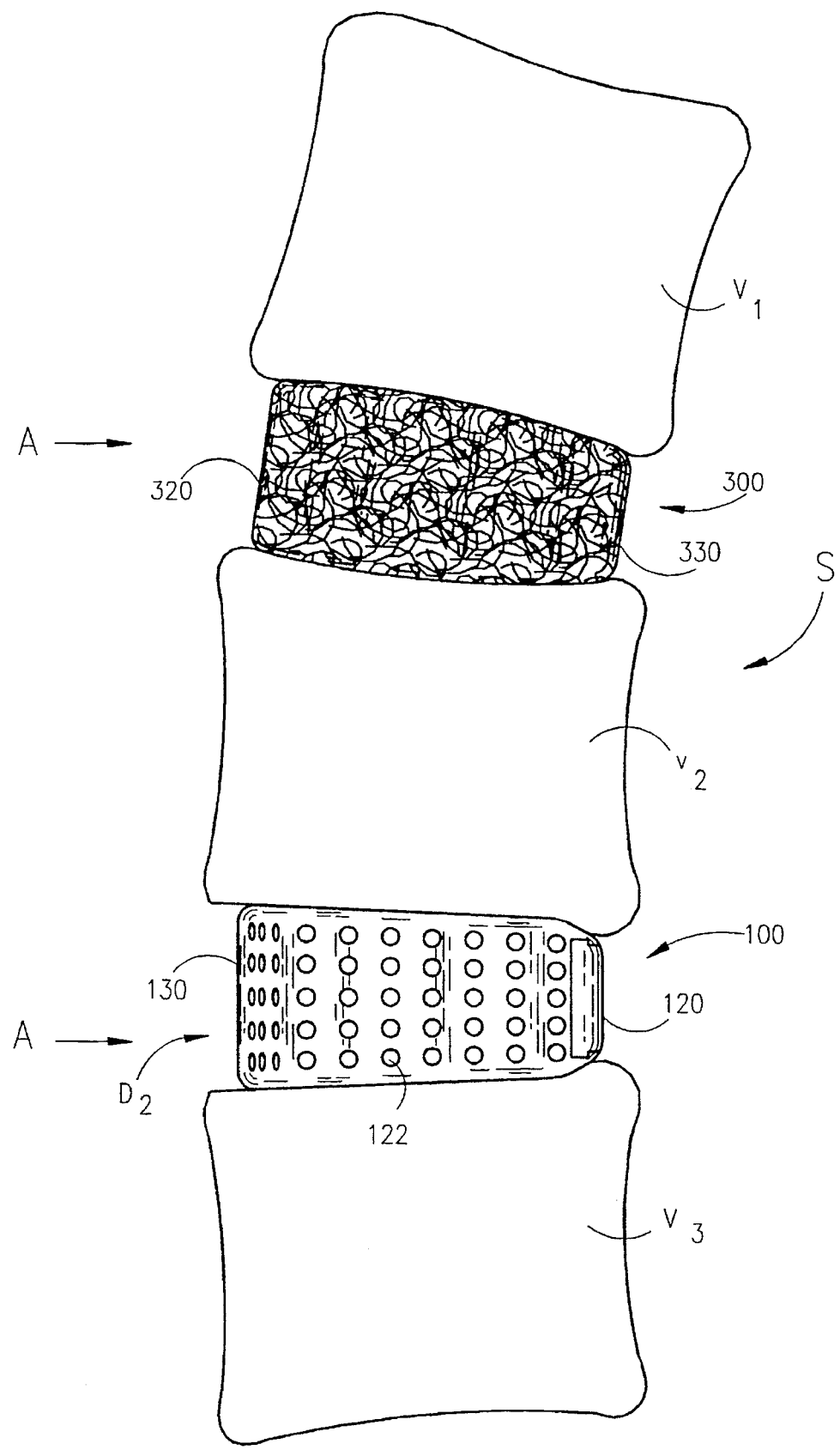
FIG. 7A is an elevational side view of a segment of the spinal column having the lordotic implant of the present invention inserted in the disc space at different disc levels between adjacent vertebrae to restore and maintain the correct anatomical alignment of the adjacent vertebrae.
Figure 26:
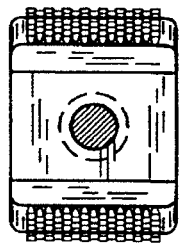
FIG. 26 is a rear end view of the lordotic interbody spinal fusion implant of FIG. 24.
Figure 25:
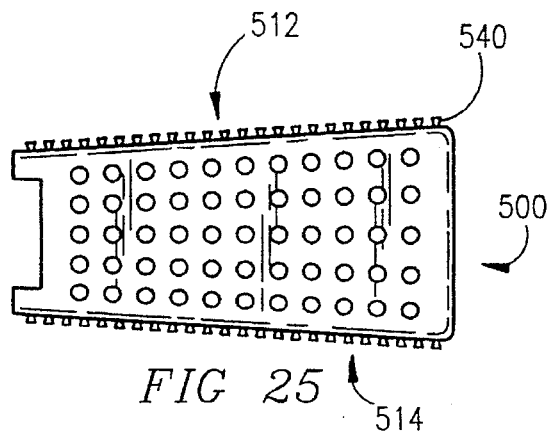
FIG. 25 is a left side elevational view of the lordotic interbody spinal fusion implant of FIG. 24.
Figure 27:
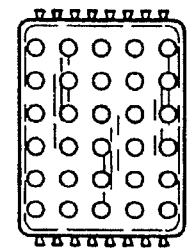
FIG. 27 is a front end view of the lordotic interbody spinal fusion implant of FIG. 24.

Referring to FIG. 7A, a side elevational view of the lateral aspect of a segment of the spinal column S is shown with the implant 100 inserted in the disc space $D_2$ between two adjacent vertebrae $V_2$ and $V_3$. The implant 100 is inserted in the direction of arrow A into the disc space $D_2$ and maintains the two vertebrae $V_2$ and $V_3$ in angular relationship to each other such that the natural lordosis of that segment of the spinal column S is restored. The forward advancement of the implant 100 is blocked by the natural bone processes B in the endplates of the vertebrae $V_2$ and $V_3$. Backing out of the implant 100 is prevented by the bone engaging surface knurling 121 of the upper and lower surfaces 112 and 114.

Referring to FIGS. 8–12, an alternative embodiment of the lordotic interbody spinal fusion implant of the present invention, generally referred to by the numeral 200, is shown. The implant 200 has a similar overall configuration as the implant 100 described above. In the preferred embodiment, the implant 200 is solid and comprises a plurality of channels 215 passing from the upper surface 212 to the lower surface 214 through the implant 200. The channels 215 provide for bone ingrowth and facilitate the incorporation of the implant 200 into the spinal fusion mass. The channels may also be loaded with fusion promoting materials such as those described above, prior to implantation. It is appreciated that the channels 215 need not pass all the way through the implant 200, but can have a configuration similar to wells, which may hold fusion promoting materials and permit bone ingrowth into the upper and lower surfaces 212 and 214 of the implant 200.

In addition to the channels 215, the implant 200 may have small openings 222 on the side wall 218 which may or may not pass through the entire implant 200. The same openings 222 may be in communication with the channels 215 such that bone ingrowth may occur from the openings 222 to the channels 215 to lock the implant 200 into the fusion mass. If the openings 222 do not pass through the entire implant 200, the may function as small wells for holding fusion promoting materials or described above.

In the preferred embodiment of implant 200, the channels 215 have a diameter in the range of 0.1 mm to 6 mm, with 2–3 mm being the preferred diameter. The openings 222 have a diameter in the range of 0.1 mm to 6 mm, with 1–3 mm being the preferred diameter range. It is appreciated that although the channels 215 and openings 222 are shown having a generally rounded configuration, it is within the scope of the present invention that the channels 215 and openings 222 may have any size, shape, configuration, and distribution suitable for the intended purpose.

The implant 200, has a plurality of ratchetings 250 on the upper and lower surface 212 and 214 for engaging the bone of the adjacent vertebrae. The ratchetings 250 comprise a bone engaging edge 252 and angled segment 254.

Referring specifically to FIG. 9, the implant 200 has a wedge-shaped elevational side view in which the trailing end 230 is taller than the insertion end 220. The plurality of ratchetings 250 are oriented in the direction of the insertion end 220 to provide for a one-way insertion of the implant 200 as the bone engaging edge 252 engages the vertebrae and prevents the implant from backing out once implanted.

Alternatively, the trailing end ratchetings could be of a lessor height such that the overall shape of the ratchetings as a group is convex.

Referring to FIG. 11, the trailing end 230 of implant 200 has means for engaging insertion instrumentation comprising a thread opening 226 as described above for implant 100.

Referring to FIG. 12, an enlarged fragmentary view along line 12 of FIG. 8 illustrating the surface configuration the implant 200 is shown. The upper and lower surfaces 212 and 214 of implant 200, in addition to the ratcheting 250 comprise a porous texture 260 to present an irregular surface to the bone to promote bone ingrowth. The porous texture 260 is also able to hold fusion promoting materials and provides for an increased surface area to engage the bone in the fusion process and to provide further stability. The porous texture 260 may also be present on the side walls 218. It is appreciated that the outer surface and/or the entire implant 200, may comprise any other porous material or roughened surface sufficient to hold fusion promoting substances and/or allow for bone ingrowth and/or engage the bone during the fusion process. The implant 200 may be further coated with bioactive fusion promoting substances including, but not limited to, hydroxyapatite compounds, osteogenic proteins and bone morphogenic proteins.

Referring to FIGS. 13–17, an alternative embodiment of the lordotic interbody spinal fusion implant, generally referred to by the numeral 300, is shown. The implant 300 is made of a mesh-like material comprising strands, which may be made of metal, that are pressed together and molded. The upper and lower surfaces 312 and 314 may be convex and conform to the natural surface curvature of the end plates of the vertebrae. In addition, the entire implant 300 may be molded to a shape that conforms to the shape of the disc space created by the removal of disc material from between two adjacent vertebrae. In this manner, the implant 300 has curved upper and lower surfaces 312 and 314, a curved side wall 318 and chamfered edges 319.

Referring to FIG. 7A, the implant 300 is shown inserted in the direction of arrow A into the disc space $D_1$ between adjacent vertebrae $V_1$ and $V_2$. The implant 300 conforms to the endplates of the adjacent vertebrae $V_1$ and $V_2$ as the upper and lower surfaces 312 and 314 are convex, and the side walls 318 are curved to conform to the natural curvature of the vertebrae $V_1$ and $V_2$. In this manner, the implant 300 has the same dimensions as the disc material removed from between the two adjacent vertebrae $V_1$ and $V_2$.

The implant 300 may be made wholly or in part of a solid material and/or a porous material, and/or a mesh-like material. The implant 300 may have a surface comprising of a porous material, a mesh-like material, or have a surface that is roughened. It is appreciated that the implant 300 may be solid or may be partially hollow and include at least one internal chamber in communication with said upper and lower surfaces.

As shown in FIG. 17, the mesh-like material comprises strands that are formed and pressed together such that interstices 339, capable of retaining fusion promoting material and for allowing for bone ingrowth, are present between the strands in at least the outer surface of implant 300. Alternatively, it is appreciated that the implant 300 may be made of a cancellous material, similar in configuration to human cancellous bone, having interstices allowing for bone ingrowth. As the implant 300 may be made entirely or in part of the cancellous material, the interstices may be present in the outer surface of the implant 300 and/or within the entire implant to promote bone ingrowth and hold bone fusion promoting materials.

Referring to FIGS. 18–23 an alternative embodiment of the implant of the present invention, generally referred to by the numeral 400, is disclosed. The implant 400 has a substantially rectangular shape having upper and lower surfaces 412 and 414. The upper and lower surfaces 412 and 414 support the adjacent vertebrae and are disposed in a converging angular relationship to each other in the same manner described above.

The implant 400 has a width W that is substantially less than the width of the implants 100–300 such that a series of such implants 400 are used as the interbody spinal implant, each placed closely adjacent to one another to approximate the size of the removed disc. The size of the implant 400 is approximately 26 millimeters in length and is wide enough so that four of them will substantially fill the intervertebral space, depending on which vertebrae are fused.

In the performing of a posterior lumbar interbody fusion, it is not possible to replace the removed portions of the disc, if a total nuclear discectomy has been performed, with a single large implant as the delicate dural sac containing the spinal cord and nerve roots covers at all times at least some portion of the posterior disc space. The use of modular implants 400 that are inserted separately into the disc space is appropriate in such case. The modular implants 400 being approximately as long as the depth of the disc material removed, but being considerably narrower, such that they could be introduced into the disc space from the posterior aspect to either side of the dural sac, and then realigned side to side with the disc space so that a number of them each having a length consistent with the depth of the disc removed in that area would in combination have a width equal to the width of the disc material removed. As the disc spaces in the lumbar spine are generally lordotic, the insertion end 420 of the modular implants 400 would have to be taller and less tall posteriorly at the trailing end 430.

To introduce the modular implant 400 that is taller at its insertion end 420 than the space available at the posterior aspect of the disc space, even when that disc space is optimally distracted, is problematic. The modular implants 400 of provide two solutions to the problem. The modular implants 400 may have a reduced size at their insertion end 420, including but not limited to, a bullet nose, a convexity, and a chamfer to a smaller front surface. This then provides that the implant 400 has an area small enough to be introduced into the posterior aspect of the disc space when the disc space is adequately distracted and the contour of that specialized insertion end of the implant 400 is such that it then allows for a ramping up of the adjacent vertebrae relative to the implant 400 as the implant is advanced forward into the disc space.

Alternatively, or in combination with the above, since in the preferred embodiment the implants 400 are wedge-shaped in the side elevational view when upright but are generally rectangular when viewed from the top plan view, these implants may be introduced into the disc space on their side such that the side walls of the implants are adjacent to the end plates of the adjacent vertebrae. The implants 400 have a side-to-side dimension that is less than the dimension through the insertion end of the implant 400 when upright. It is possible to easily insert the implant 400 first on their side and then to use the insertion instrument engaged to the implant 400 to rotate the implant ninety degrees into the fully upright position, once it has been fully inserted. Once inserted, the upper and lower surfaces 412 and 414 are adjacent to the endplates of the adjacent vertebrae and create and maintain the desired angular relationship of the adjacent vertebrae as the upper and lower surfaces 412 and 414 of the implant 400 are angled with respect to each other.

The implant 400 has large openings 415 in the form of rectangular slots for holding fusion promoting materials to promote bone growth from the vertebrae through the upper and lower surfaces 412 and 414 and into the interior of the implant 400. As the implant 400 is modular and more than one is implanted at a time, the large openings 415 are also present in the side walls 418 of the implant 400 to provide for bone growth from one implant to another implant such that after successful fusion, the modular implants 400 are interconnected to form a single unit.

Referring to FIG. 21, the trailing end 430 of the implant 400 is shown having an insertion instrument engaging means comprising a rectangular slot 424 and threaded opening 426.

Referring to FIG. 23, an enlarged fragmentary view along line 23 of FIG. 18 illustrating the surface configuration the implant 400 is shown. The surface configuration of the implant 400 is the same as the porous texture 260 described above.

Figure 24:
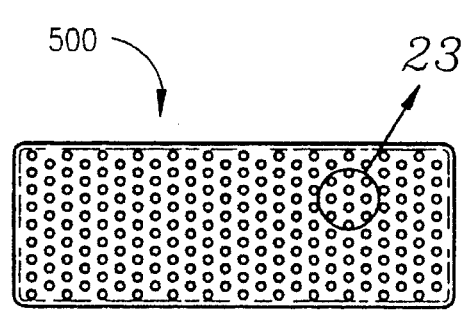
FIG. 24 is a top plan view of an alternative embodiment of the lordotic interbody spinal fusion implant of the present invention.

Referring to FIG. 24, an alternative embodiment of the lordotic interbody spinal fusion implant of the present invention, generally referred to by the numeral 500, is shown. The implant 500 is a modular implant and has a similar overall configuration as implant 400. The implant 500 instead of having slots 415 has an upper and lower surfaces 512 and 514 that are capable of receiving and holding bone, or other materials capable of participating in the fusion process and/or capable of promoting bone ingrowth. In the preferred embodiment, the upper and lower surfaces 512 and 514 comprise a plurality of posts 540 that are spaced apart to provide a plurality of interstices 542 which are partial wells with incomplete walls capable of holding and retaining milled bone material or any artificial bone ingrowth promoting material. The implant 520 may be prepared for implantation by grouting or otherwise coating the surface 538 with the appropriate fusion promoting substances.

Figure 28:
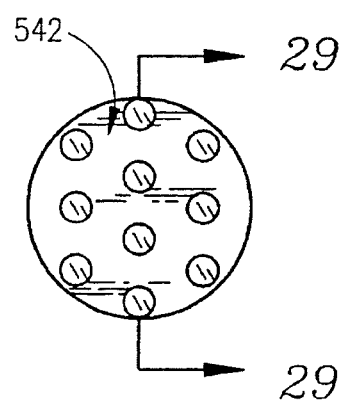
FIG. 28 is an enlarged fragmentary view along line 28 of the lordotic interbody spinal fusion implant of FIG. 24 illustrating the surface configuration of the lordotic interbody spinal fusion implant of the present invention.
Figure 29:
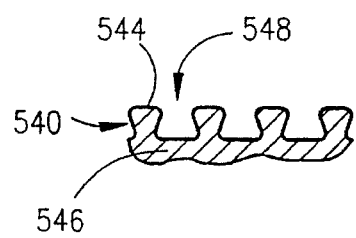
FIG. 29 is a sectional view along lines 29—29 of FIG. 28 the lordotic interbody spinal fusion implant of the present invention.

Referring to FIG. 28 and 29, an enlarged view of the upper surface 512 of the implant 500 and a partial cross section thereof are shown. In the preferred embodiment, the posts 540 have a head portion 544 of a larger diameter than the remainder of the posts 540, and each of the interstices 542 is the reverse configuration of the posts 544, having a bottom 546 that is wider than the entrance 548 to the interstices 542. Such a configuration of the posts 540 and interstices 542 aids in the retention of bone material in the surface 538 of the implant 520 and further assists in the locking of the implant 520 into the bone fusion mass created from the bone ingrowth. As the bone ingrowth at the bottom 546 of the interstices 542 is wider than the entrance 548, the bone ingrowth cannot exit from the entrance 548 and is locked within the interstice 542. The surface 538 of the implant 520 provides for an improvement in the available amount of surface area which may be still further increased by rough finishing, flocking or otherwise producing a non smooth surface.

In the preferred embodiment, the posts 540 have a maximum diameter in the range of approximately 0.1–2 mm and a height of approximately 0.1–2 mm and are spaced apart a distance of approximately 0.1–2 mm such that the interstices 542 have a width in the range of approximately 0.1 to 2 mm. The post sizes, shapes, and distributions may be varied within the same implant.

It is appreciated that the implant 500 shares the same structure and features of the implant 400 described above.

Figure 30:
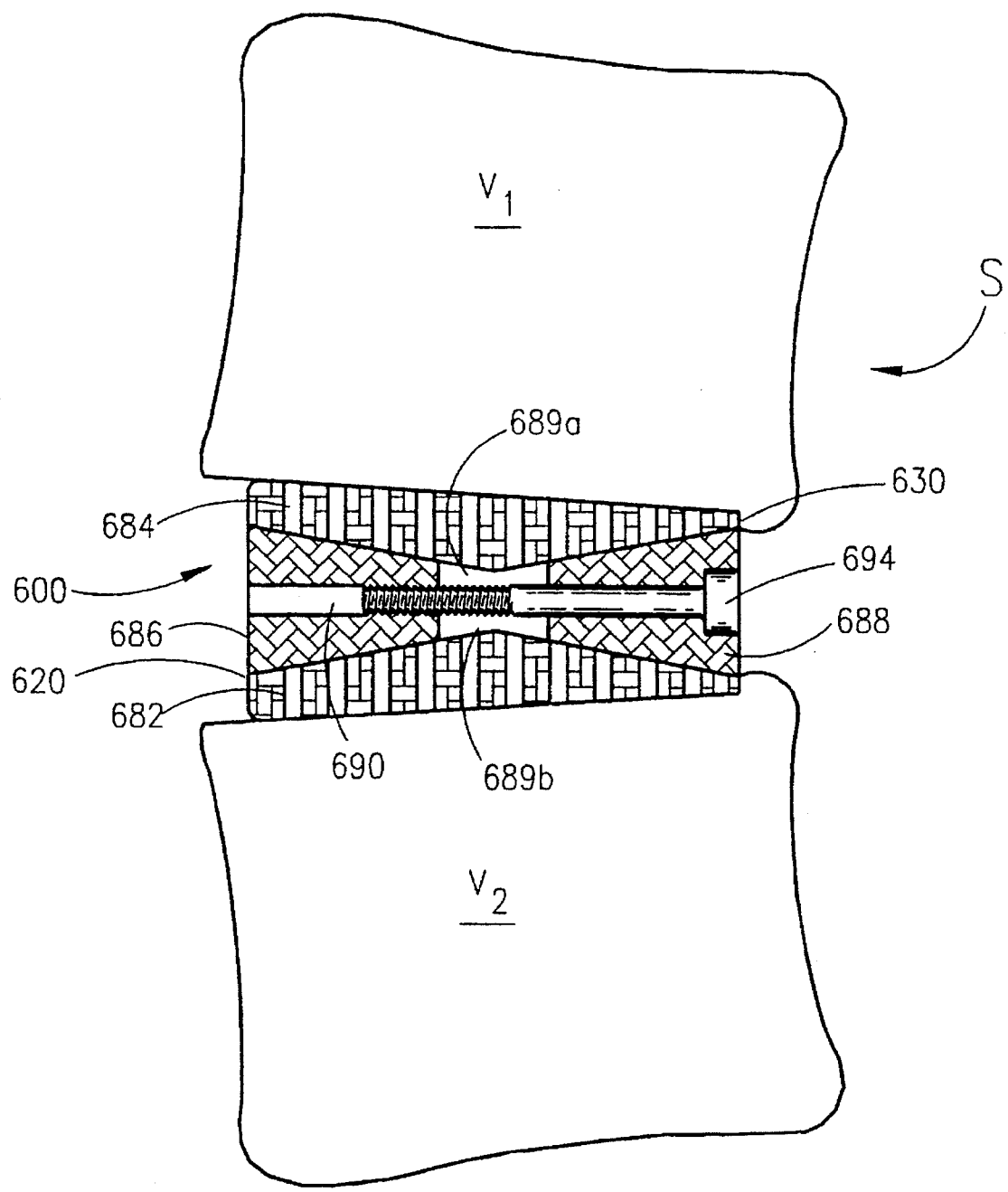
FIG. 30 is a side elevational view of a segment of the human spinal column shown with an alternative embodiment of the lordotic spinal fusion implant of the present invention that is adjustable and expandable shown in sectional view inserted in the disc space levels to restore and maintain the correct anatomical alignment of the adjacent vertebrae.

FIG. 30 is a side elevational view of a segment of the human spinal column S shown in lordosis with an alternative embodiment of the lordotic spinal fusion implant referred to by the numeral 600, that is adjustable and expandable shown inserted in a space to restore and maintain the correct anatomical alignment of the adjacent vertebrae. The implant 600 comprises a lower member 682 and an upper member 684 which when fitted together form an essentially rectangular implant. The upper member 684 and the lower member 682 have hollow portions that face one another and receive tapered wedges 686 and 688 that fit within the hollow portion of the upper and lower members 682 and 684. The upper and lower members 682 and 684 each have a wedged interior surface 689a and 689b which are angled towards the interior of the implant 600. The wedges 682 and 684 are such that at their large end, they are higher than the combined hollow space between the upper and lower members 684 and 682, and shallower at the other end than the hollow space between the upper and lower members.

The wedges 686 and 688 have a central threaded opening 690 and 692 in alignment with each other for receiving threaded screw 694. As the screw 694 is threaded into the opening 690, the wedges 686 and 688 abut the interior sloped surfaces 689a and 689b of the upper and lower members 682 and 684. As the screw 694 is turned, the wedges 686 and 688 are drawn together, and the sloped portions of the wedges force the upper member 682 away from the lower member 684. As the interior sloped surfaces 689a and 689b have a greater slope near the trailing end 630, than near the insertion end 620, the upper and lower members 682 and 684 are forced apart more at the insertion end 620 than at the trailing end 630. As a result, the upper and lower members 682 and 684 are disposed at a converging angular relationship to each other and support the adjacent vertebrae $V_1$ and $V_2$ in the same angular relationship.

Figure 31:
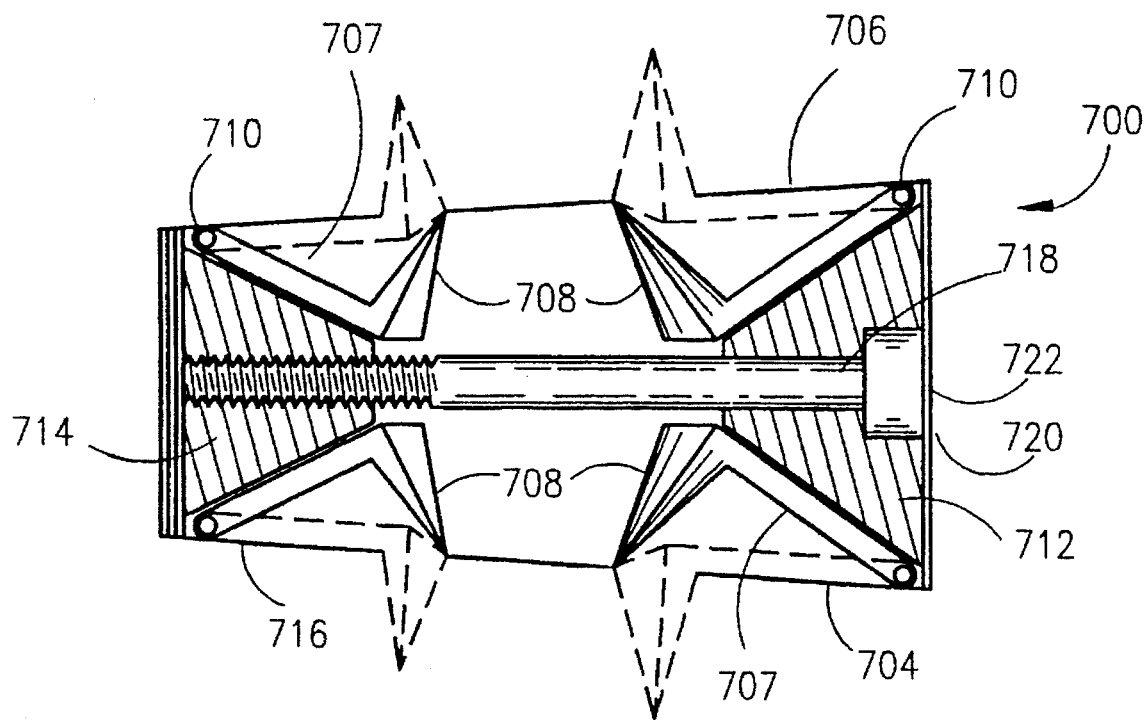
FIG. 31 is a side cross sectional view of an alternative embodiment of the lordotic implant of the present invention having movable projections, in the form of spikes 708, which are movable from a first position within the implant 700 to a second position extending to the exterior of the implant.
Figure 32:
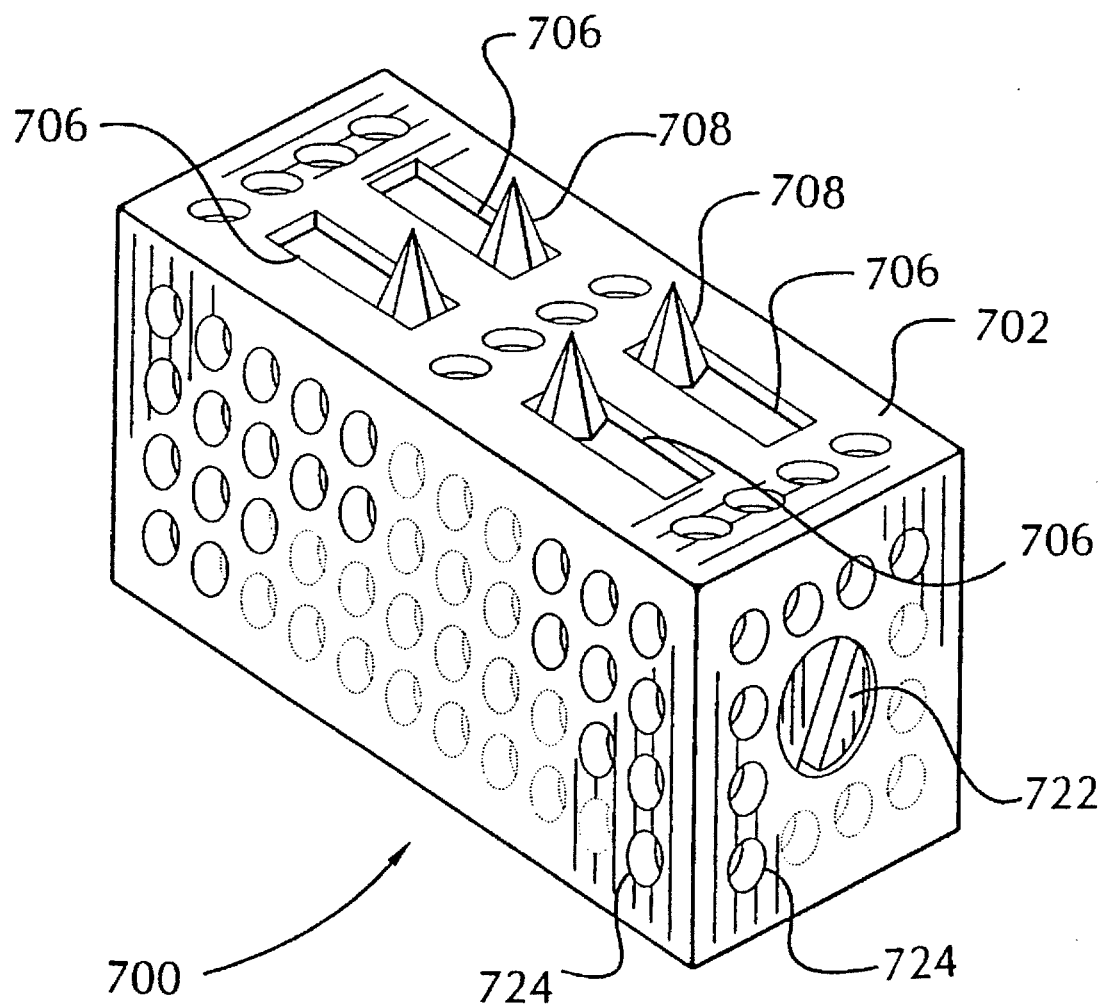
FIG. 32 is a perspective view of the implant of FIG. 31.

Referring to FIG. 31, an alternative embodiment of the implant of the present invention, generally referred to by the numeral 700, is shown. The implant 700 has movable projections, in the form of spikes 708, which are movable from a first position within the implant 700 to a second position extending outside of the implant. The implant 700 is of a generally rectangular configuration, having a top surface 702 and a bottom surface 704 of the implant with slots 706 for permitting pivotal member 707 having spikes 708 at their ends to project through said slots 706. The spikes 708 are pinned at one end 710 within the implant 700.

The implant 700 has opposing wedge shaped members 712 and 714 having a central threaded opening 716 for receiving a threaded screw 718 having a head 720 and a slot 722. The wedges 712 and 714 are facing each other so that upon turning of the screw 718, will the two wedges 712 and 714 are drawn together to cause the spikes 708 to pivot about their end 710 and project to the exterior of the implant 700 through the aligned slots 706. The implant 700 may comprise a series of holes in the upper and lower surfaces 702 and 704 for promoting bone ingrowth and fusion.

In use, after the removal of the disc material, the implant 700 with the spikes 708 in their withdrawn position, is inserted into the disc space. Then the screw 718 is turned until the spikes 708 are forced to enter the vertebrae and the implant 700 is thus held firmly in place.

While the invention has been described with regards to the preferred embodiment and a number of alternative embodiments, it is recognized that other embodiments of the present invention may be devised which would not depart from the scope of the present invention.

What is claimed is:

1. An interbody spinal fusion implant for fusion of two adjacent vertebrae in the human spine in which said implant to be interposed between the vertebral endplates of said adjacent vertebrae, comprising:

upper and lower walls, insertion and trailing walls, and side walls;

a plurality of openings in at least said upper and lower walls, at least some of said plurality of openings allowing for communication between said upper wall and said lower wall so as to be capable of containing fusion promoting materials for promoting bone ingrowth is continuity through said implant from the vertebral endplate of one of said adjacent vertebrae to the vertebral endplate of the other of said adjacent vertebrae for fusion of said adjacent vertebrae;

said upper and lower walls forming a support structure including at least a portion of the surfaces of said upper and lower walls between said plurality of openings and between said insertion, trailing, and side walls for bearing against the vertebral endplates of the adjacent vertebrae, said upper and lower walls being disposed at least in part in a diverging angular relationship to each other from said insertion wall to said trailing wall, said upper and lower walls being spaced apart at a distance from each other that is greater at said trailing wall than at said insertion wall;

whereby the insertion of said implant between the vertebral endplates of the two adjacent vertebrae supports the two adjacent vertebrae in an angular relationship and allows for bone growth to occur through said implant from one vertebral endplate adjacent to said implant to the other vertebral endplate adjacent to said implant.

2. The implant of claim 1 in which the depth of said implant is substantially the same as the depth of a space created by the removal of the nucleus pulposus from between the two adjacent vertebrae.

3. The implant of claim 1 in which the width of said implant is substantially equal to the transverse width of a space created by the removal of the nucleus pulposus from between the two adjacent vertebrae.

4. The implant of claim 1 in which said implant has substantially the same height, width and depth as a space created by the removal of at least generally the nucleus pulposus and at least a portion of the annulus fibrosus from between the two adjacent vertebrae.

5. The implant of claim 1 in which said implant has substantially the same shape as a space created by the removal of at least a substantial portion of the nucleus pulposus and a portion of the annulus fibrosus from between the two adjacent vertebrae.

6. The implant of claim 1 in which said upper wall has a fixed shape which is generally configured to match the contours of the endplate of one of the two adjacent vertebrae.

7. The implant of claim 1 in which said lower wall has a fixed shape which is generally configured to match the natural contours of the endplate of one of the two adjacent vertebrae.

8. The implant of claim 1 in which said upper wall has a fixed shape which is generally configured to match the natural contours of the endplate of a first of the two adjacent vertebrae, and said upper wall has a fixed shape which is generally configured to match the natural contours of the endplate of a second of the two adjacent vertebrae.

9. The implant of claim 1 in which at least a portion of said insertion wall is tapered for facilitating insertion of the implant between the two adjacent vertebrae.

10. The implant of claim 1 in which said implant comprises an insertion end and a trailing end, said insertion end comprising at least one tapered portion.

11. The implant of claim 1 in which said insertion wall is convex and conforms to a space created by the removal of at least generally the nucleus pulposus and a portion of the annulus fibrosus from between the two adjacent vertebrae.

12. The implant of claim 1 in which said trailing wall is curved.

13. The implant of claim 12 in which said trailing wall is convex.

14. The implant of claim 1 in which said side walls are curved.

15. The implant of claim 1 in which the shape of said side walls is generally trapezoidal.

16. The implant of claim 1 in which said implant is substantially rectangular.

17. The implant of claim 1 in which at least some of said openings are approximately 1 mm to 3 mm in diameter.

18. The implant of claim 1 in which at least some of said plurality of openings are greater than microscopic in size.

19. The implant of claim 1 in which at least a portion of said plurality of openings are microscopic in size.

20. The implant of claim 1 in which at least some of said plurality of openings pass through said upper and said lower walls forming a plurality of channels through said implant.

21. The implant of claim 1 in which said implant has at least one interior chamber and having at least one of said plurality of openings in said upper wall and at least one of said plurality of openings in said lower wall being in communication with said at least one interior chamber.

22. The implant of claim 21 in which said implant includes an access opening for accessing said at least one interior chamber, said access opening being larger than the largest of said plurality of openings.

23. The implant of claim 22 including a covering means for closing said access opening.

24. The implant of claim 23 in which said covering means for closing said access opening comprises a slidable door.

25. The implant of claim 1 having a plurality of openings capable of retaining fusion promoting material.

26. The implant of claim 25 in which said plurality of openings comprise wells.

27. The implant of claim 1 in which said implant includes bone engaging means for engaging said implant to adjacent vertebrae of the spine.

28. The implant of claim 27 in which said bone engaging means includes a plurality of surface roughenings for engaging said adjacent vertebrae and for maintaining said implant in place, said surface roughenings being present on at least a portion of said upper and lower walls.

29. The implant of claim 28 in which said surface roughenings comprises a plurality of ridges.

30. The implant of claim 29 in which said a plurality of ridges are facing the direction of insertion for preventing said implant from backing out once inserted between said adjacent vertebrae.

31. The implant of claim 28 in which said surface roughenings comprise at least one groove.

32. The implant of claim 28 in which said surfaces roughenings comprise a plurality of spike projections.

33. The implant of claim 32 in which said implant includes means for retracting and extending said plurality of spike projections.

34. The implant of claim 28 in which said surface roughenings include knurling.

35. The implant of claim 1 in which said implant comprises a mesh-like material having a plurality of interstices for receiving fusion promoting material.

36. The implant of claim 1 in which said implant has an exterior surface that is porous at least in part.

37. The implant of claim 1 in which said implant has at least a portion of its surface treated to promote bone ingrowth between said surface and a vertebrae.

38. The implant of claim 1 in which said implant comprises a bone ingrowth material for promoting bone ingrowth between said implant and said two adjacent vertebrae.

39. The spinal fusion implant of claim 1 in which said implant is at least in part bioabsorbable.

40. The implant of claim 1 in which said implant includes driving engaging means for engaging a driving instrument for implanting said implant within the disc space between the two adjacent vertebrae.

41. The implant of claim 1 which said implant comprises a plurality of modular members, each of said modular members having a height substantially equal to the height of the space created by the removed disc material from between two adjacent vertebrae and a width substantially less than the transverse width of the vertebrae.

42. The implant of claim 1 in which said implant dimensionally corresponds to the space created by the removal of at least generally all of the nucleus pulposus and a portion of the annulus fibrosus when said adjacent vertebrae are distracted and placed in angular relationship to each other.

43. The implant of claim 1 for use in the cervical spine in which the depth of said implant is in the range of approximately 11 mm to 21 mm.

44. The implant of claim 1 for use in the cervical spine in which the width of said implant is in the range of approximately 14 mm to 28 mm.

45. The implant of claim 1 for use in the cervical spine in which said implant has a height in the range of approximately 5 mm to 10 mm, a width in the range of approximately 14 mm to 28 mm, and depth in the range of approximately 11 mm to 21 mm.

46. The implant of claim 1 for use in the lumbar spine in which the depth of said implant is in the range of approximately 20 mm to 34 mm.

47. The implant of claim 1 for use in the lumbar spine in which the width of said implant is in the range of approximately 28 mm to 48 mm.

48. The implant of claim 1 for use in the lumbar spine in which said implant has a height in the range of approximately 8 mm to 16 mm, a width in the range of approximately 28 mm to 48 mm, and depth in the range of approximately 20 mm to 34 mm.

49. The implant of claim 1 including expanding means for moving said upper and lower walls apart in said diverging angular relationship.

50. An interbody spinal fusion implant for fusion of two adjacent vertebrae in the human spine in which said implant to be interposed between the vertebral endplates of said adjacent vertebrae, comprising:

upper and lower walls, insertion and trailing walls, and side walls, said upper and lower walls forming a support structure including at least a portion of the surfaces of said upper and lower walls between said insertion, trailing and side walls for conforming to and bearing against the vertebral end plates of the adjacent vertebrae;

said upper and lower wall being disposed at least in part in a diverging angular relationship to each other, said upper and lower walls being spaced apart at a distance from each other that is greater at said trailing wall than at said insertion wall; and means for permitting bone ingrowth through said implant for fusion of said adjacent vertebrae;

whereby the insertion of said implant between the vertebral endplates of the two adjacent vertebrae supports the two adjacent vertebrae in an angular relationship and allows for bone growth to occur through said implant from one vertebral endplate adjacent to said implant to the other vertebral endplate adjacent to said implant.

51. The implant of claim 50 in which said implant dimensionally corresponds to the space created by the removal of at least generally all of the nucleus pulposus and a portion of the annulus fibrosus when said adjacent vertebrae are distracted and placed in angular relationship to each other.

* * * * *